United States Patent
Yoshida

(10) Patent No.: US 10,426,715 B2
(45) Date of Patent: Oct. 1, 2019

(54) LIPOSOME COMPOSITION

(71) Applicant: KOSE CORPORATION, Tokyo (JP)

(72) Inventor: Mitsuru Yoshida, Tokyo (JP)

(73) Assignee: KOSE CORPORATION, Tokyo (JP)

( * ) Notice: Subject to any disclaimer, the term of this patent is extended or adjusted under 35 U.S.C. 154(b) by 0 days.

(21) Appl. No.: 15/561,814

(22) PCT Filed: Mar. 24, 2016

(86) PCT No.: PCT/JP2016/059508
§ 371 (c)(1),
(2) Date: Sep. 26, 2017

(87) PCT Pub. No.: WO2016/158704
PCT Pub. Date: Oct. 6, 2016

(65) Prior Publication Data
US 2018/0110701 A1    Apr. 26, 2018

(30) Foreign Application Priority Data
Mar. 27, 2015   (JP) ................. 2015-067342

(51) Int. Cl.

| | |
|---|---|
| *A61K 8/04* | (2006.01) |
| *A61K 8/14* | (2006.01) |
| *A61Q 19/00* | (2006.01) |
| *A61K 8/9728* | (2017.01) |
| *A61K 8/34* | (2006.01) |
| *A61K 8/55* | (2006.01) |
| *A61K 8/67* | (2006.01) |
| *A61Q 13/00* | (2006.01) |

(52) U.S. Cl.
CPC .............. *A61K 8/14* (2013.01); *A61K 8/042* (2013.01); *A61K 8/046* (2013.01); *A61K 8/345* (2013.01); *A61K 8/553* (2013.01); *A61K 8/678* (2013.01); *A61K 8/9728* (2017.08); *A61Q 13/00* (2013.01); *A61Q 19/00* (2013.01)

(58) Field of Classification Search
None
See application file for complete search history.

(56) References Cited

U.S. PATENT DOCUMENTS

| | | |
|---|---|---|
| 4,687,661 A | 8/1987 | Kikuchi et al. |
| 4,829,512 A | 5/1989 | Nakai et al. |
| 6,190,679 B1 | 2/2001 | Takekoshi et al. |
| 2013/0078294 A1 | 3/2013 | Alexiades-Armenakas |
| 2015/0202139 A1* | 7/2015 | Friedman ............. A61K 8/35 424/450 |

FOREIGN PATENT DOCUMENTS

| | | |
|---|---|---|
| JP | 60-7932 A | 1/1985 |
| JP | 61-143311 A | 7/1986 |
| JP | 63-153938 A | 6/1988 |
| JP | 8-183726 A | 7/1996 |
| JP | 11-269056 A | 10/1999 |
| JP | 2000-63265 A | 2/2000 |
| JP | 2000-229811 A | 8/2000 |
| JP | 2004-143080 A | 5/2004 |
| JP | 2004-359573 A | 12/2004 |
| JP | 2005-112742 A | 4/2005 |
| JP | 2005-330257 A | 12/2005 |
| JP | 2006-111545 A | 4/2006 |
| JP | 2006-131558 A | 5/2006 |
| JP | 2006-137684 A | 6/2006 |
| JP | 2006-182695 A | 7/2006 |
| JP | 2007-269635 A | 10/2007 |
| JP | 2007-291035 A | 11/2007 |
| JP | 2008-94809 A | 4/2008 |
| JP | 2008-127327 A | 6/2008 |
| JP | 2010-506889 A | 7/2010 |
| JP | 2010-235491 A | 10/2010 |
| JP | 2011-144133 A | 7/2011 |
| JP | 2012-72065 A | 4/2012 |
| JP | 2012-184182 A | 9/2012 |
| JP | 2014-50018 A | 1/2014 |

OTHER PUBLICATIONS

International Search Report dated Apr. 19, 2017, issued in counterpart International Application No. PCT/JP2016/059508, with English translation (5 pages).
International Preliminary Report on Patentability (Form PCT/IB/373) issued in counterpart International Application No. PCT/JP2016/059508 dated Oct. 3, 2017, with PCT/ISA/237, with English translation (14 pages).
Production of Cosmetic and Nanotechnolgy, CMC Publication Co., Ltd., Tokyo, Japan, 2007, pp. 48, 111-116; w/ partial English translation; cited in JP Third Party Observation.
Technology of Evidence Based Cosmetics, CMC Publishing Co., Ltd., Tokyo, Japan, 2004, p. 280=290; w/partial English translation; cited in JP Third Party Observation.
Fragrance Journal with English Abstract, 2005, p. 45-50; cited in JP Third Party Observation. (6 pages).
Third Party Observation dated Feb. 26, 2019, issued in counterpart JP Application No. 2017-509883. (9 pages).
Office Action dated Aug. 6, 2019 issued in the counterpart Japanese application No. 2017-509883, with English translation. (16 pages).

* cited by examiner

*Primary Examiner* — Nannette Holloman
(74) *Attorney, Agent, or Firm* — Westerman, Hattori, Daniels & Adrian, LLP

(57) ABSTRACT

The object is to develop a liposome composition showing superior persistency of moisturizing effect and superior persistency of skin firmness and tightness-imparting effect, as well as superior temporal stability of liposomes. There is provided a liposome composition containing the following ingredients (a) to (e): (a) a phospholipid, (b) a *Tremella fuciformis* extract, (c) vitamin E or a derivative thereof, (d) a polyhydric alcohol having an IOB value of 1.5 to 5, and (e) water.

6 Claims, No Drawings

LIPOSOME COMPOSITION

TECHNICAL FIELD

The present invention relates to a liposome composition. More precisely, the present invention relates to a liposome composition containing a phospholipid, a *Tremella fuciformis* extract, vitamin E or a derivative thereof, a polyhydric alcohol having an IOB value of 1.5 to 5, and water, which exhibits superior persistency of moisturizing effect and superior persistency of skin firmness and tightness-imparting effect, as well as superior temporal stability of liposomes.

BACKGROUND ART

Liposomes, which are closed vesicles consisting of bilayers of phospholipids as major constituents of biological membranes, have been used for researches as a biological membrane model, and uses thereof for drugs and cosmetics as a microcapsule for enclosing and delivering a drug have been attempted for many years. In the field of cosmetics, in particular, liposomes attract attentions, because they are valuable forms as microcapsule, and phospholipids themselves as constituents of liposomes are highly safe amphiphilic substances derived from biological membranes.

Uses and functions of liposomes have been diversified, and developments of uses for cosmetics and skin external preparations have also been attempted. From the viewpoint of beautifully showing skin, there are desired those not only having whitening effect and moisturizing effect, but also imparting firmness and tightness as well as elasticity of the skin to such an extent that the effects can be actually realized. As a result, there have been proposed techniques for preparing liposomes aiming at realizing high moisturizing effect of cosmetics and so forth by adding liposomes constituted with phospholipids to them. For example, there have been proposed liposomes containing hydrogenated soybean phospholipids having a phosphatidylcholine content not lower than 90 mass %, cholesterol, N-acylamino acid salt, and a copolymer comprising 2-methacryloyloxyethylphosphorylcholine and butyl methacrylate (for example, refer to Patent document 1).

Many techniques concerning liposomes have been examined, including not only those concerning liposomes themselves, but also those concerning cosmetics and external preparations containing liposomes. Such techniques may realize application of the usefulness of liposomes to cosmetics or skin external preparations to further increase added values of the preparations.

PRIOR ART REFERENCE

Patent Document

Patent document 1: Japanese Patent Unexamined Publication (KOKAI) No. 2012-184182

SUMMARY OF THE INVENTION

Object to be Achieved by the Invention

However, the technique of Patent document 1 may not provide sufficiently persistent moisturizing effect after application.

For the purpose of increasing firmness and tightness of skin, various hydrophilic polymer molecules and oil-soluble ingredients have been added to skin external preparations. However, although firmness and tightness can be obtained immediately after application of such external preparations, the firmness and tightness can be obtained only temporarily, and they are not sufficient yet in respect of temporal persistency of the skin firmness and tightness-imparting effect.

Means for Achieving the Object

In view of the aforementioned actual conditions, the inventor of the present invention conducted various researches aiming at developing a liposome composition that shows superior persistency of moisturizing effect and superior persistency of skin firmness and tightness-imparting effect, as well as superior temporal stability of liposomes. As a result of researches concerning ingredients that can provide skin moisturizing effect and skin firmness and tightness-imparting effect, and persistencies of the effects to such an extent that the persistencies can be actually realized, when the ingredients are added to a conventional liposome composition consisting of a phospholipid, a polyhydric alcohol, and water, it was found that if both of a *Tremella fuciformis* extract and vitamin E or a derivative thereof are added, persistencies of the effects can be obtained, which persistencies of the effects cannot be obtained by addition of one of them. As a result of researches further conducted, a liposome composition effective for all the items, persistency of moisturizing effect, persistency of skin firmness and tightness-imparting effect, and temporal stability of liposomes, could be obtained by using a polyhydric alcohol having a specific IOB value, and the present invention was accomplished.

It was also found that when a cosmetic product containing the liposome composition is prepared, the effect of the present invention can be enhanced by adding a water-soluble polymer as an aqueous ingredient serving as a dispersion medium.

The present invention thus relates to a liposome composition containing the following ingredients (a) to (e).
(a) A phospholipid
(b) A *Tremella fuciformis* extract
(c) Vitamin E or a derivative thereof
(d) A polyhydric alcohol having an IOB value of 1.5 to 5
(e) Water The present invention also relates to the liposome composition, wherein mass ratio of the ingredients (b) and (c) ((b)/(c)) contained in the liposome composition is in the range of 0.05 to 9.

The present invention also relates to the liposome composition, which further contains a lysophospholipid as an ingredient (f).

The present invention also relates to the liposome composition, wherein the ingredient (d) consists of one or two or more kinds of ingredients selected from 1,3-butyrene glycol, glycerin, and dipropylene glycol.

The present invention also relates to a cosmetic product containing the liposome composition.

The present invention also relates to the cosmetic product, wherein the cosmetic product consists of an oil-in-water type emulsion, and contains a water-soluble polymer (other than the ingredient (b)) as an ingredient (g) in an aqueous layer as a continuous phase.

The present invention also relates to the liposome composition, wherein the ingredient (a) contains a phospholipid derived from sunflower.

Effect of the Invention

The liposome composition and the aqueous cosmetic product containing the liposome composition of the present invention show superior persistency of moisturizing effect and superior persistency of skin firmness and tightness-imparting effect, as well as superior temporal stability of liposomes.

Modes for Carrying Out the Invention

Hereafter, the present invention will be specifically explained mainly for preferred embodiments thereof. The ranges indicated with "to" in this description mean ranges including the numerical values mentioned before and after "to".

The ingredient (a), phospholipid, used in the present invention has a structure that an aliphatic acid and phosphoric acid bind to glycerin or sphingosine as the main base structure, and an alcohol further binds to the phosphoric acid via an ester bond, and there are many kinds of phospholipids usable as the ingredient (a) occurring due to difference of types of the aliphatic acid, alcohol, and so forth. In the present invention, the ingredient (a) is contained as the main ingredient that forms a bimolecular lipid membrane in the liposome composition. Such an ingredient (a), phospholipid, is not particularly limited, and those used for ordinary cosmetics can be used. Examples include, for example, glycerophospholipids such as phosphatidylcholine (namely, lecithin), phosphatidylethanolamine, phosphatidylserine, phosphatidylinositol, phosphatidylglycerol, diphosphatidylglycerol, and phosphatidic acid, and one or two or more kinds of these can be used independently or as a mixture. Examples of the ingredient (a) used for the present invention include those derived from soybean, egg yolk, sunflower, or cone. Among these, those derived form sunflower are especially preferred in respect of showing persistency of the skin firmness and tightness-imparting effect. As for the term "derived from" used above, the method for extracting a certain ingredient from the origin thereof is not particularly limited, so long as the origin of the ingredient is the origin mentioned after the term "derived from".

In the present invention, the liposome composition preferably contains a phospholipid derived from sunflower, and the content thereof is preferably 20 mass % or higher, further preferably 40 mass % or higher, based on the total phospholipid amount.

The ingredient (a), phospholipid, may be a purified phospholipid, or contain a hydrogenated phospholipid (for example, hydrogenated soybean phospholipid). However, in the present invention, the ingredient (a) containing both a non-hydrogenated phospholipid and a hydrogenated phospholipid is preferred in respect of not only persistency of the moisturizing effect, but also persistency of the skin firmness and tightness-imparting effect, compared with one containing only one of them. Although the ratios of these phospholipids contained in the ingredient (a) are not particularly limited, content of the non-hydrogenated phospholipid is 0 mass % or higher, preferably 20 mass % or higher, more preferably 50 mass % or higher, based on the total phospholipid amount. Specific examples of commercial products usable as the ingredient (a) include Lecinol S-10E, Lecinol S-10EZ (these are from Nikko Chemicals Co., Ltd.), HSL-70 (YMC Co., Ltd.), Basis LS-60HR (Nisshin Oillio Group, Ltd.), Egg Yolk Lecithin PL-100P (Kewpie Corporation), Milk Ceramide 1G, Milk Ceramide 4G (these are from Yamakawa Co., Ltd.), LIPOID P 75, LIPOID P 100 (these are from Lipoid Co., Ltd.), and so forth.

A phospholipid mixed beforehand with cholesterol and/or phytosterol may also be used. Examples of commercial products of such a phospholipid include Presome CS2-101, Phytopresome, Phytocompo-PP, Composite-PC (all of these are from Nippon Fine Chemical Co., Ltd.), and so forth.

Although content of the ingredient (a) in the liposome composition of the present invention is not particularly limited, it is preferably 0.004 to 10 mass % (henceforth mass % is indicated simply as %), and more preferably 0.04 to 5%. With a content of the ingredient (a) in this range, a liposome composition showing superior skin moisturizing effect and temporal stability can be obtained.

The ingredient (b), *Tremella fuciformis* extract (shirokikurage extract, snow fungus extract), used for the present invention means a substance extracted from a fungus belonging to the family Tremellaceae by using a solvent. In the present invention, this ingredient can be expected to contribute to the skin moisturizing effect, and stabilization of liposomes. The INCI name (international indication name of cosmetic ingredient according to The International Nomenclature of Cosmetic Ingredients of The Cosmetic, Toiletry, and Fragrance Association of the United States) of the ingredient (b), *Tremella fuciformis* extract, is *Tremella fuciformis* (mushroom) extract, and INCI defines that *Tremella fuciformis* (mushroom) extract is the extract of mushroom, *Tremella fuciformis*. The ingredient (b), *Tremella fuciformis* extract, may be also referred to as *Tremella fuciformis* extractive, *Tremella fuciformis* polysaccharides, or water-soluble polysaccharides extracted from *Tremella fuciformis*.

Examples of the extraction solvent include water, lower alcohols such as ethanol, polyhydric alcohols such as 1,3-butylene glycol and dipropylene glycol, and so forth. These solvents can be used independently, or as a mixture of two or more kinds of them. Among these, it is preferable to use water or a mixture of water and a solvent miscible with water at an arbitrary ratio such as ethanol and 1,3-butylene glycol.

Although the extraction method is not particularly limited, examples include, for example, a method of mixing an extraction solvent and *Tremella fuciformis* fruiting bodies (dried material may also be used), and performing extraction with warming. The obtained extract can be used as it is, or a product obtained from the extract by appropriate concentration, or powder obtained from the extract by spray drying, lyophilization, or the like can also be used.

The ingredient (b), *Tremella fuciformis* extract, described above is not particularly limited, and examples of commercial product usable as the ingredient (b) include Tremoist-TP, Tremoist-SL (Nippon Fine Chemical Co., Ltd.), WHITE JELLY FUNGUS EXTRACT-P (Oryza Oil & Fat Chemical Co., Ltd.), and so forth.

Although content of the ingredient (b) in the liposome composition of the present invention is not particularly limited, it is preferably 0.0001 to 1.0%, more preferably 0.0005 to 0.5%, as concentration of dried pure substance, in respect of obtaining a liposome composition showing superior skin moisturizing effect.

The ingredient (c), vitamin E or a derivative thereof, used for the present invention is such a substance as described below. There are 4 kinds of homologues of vitamin E, $\alpha$, $\beta$, $\gamma$, and $\delta$, occurring due to difference of substitution patterns of methyl groups on the chroman ring, for each of the two kinds of vitamin E, tocopherol and tocotrienol, occurring due to difference of the phytyl side chains, thus 8 kinds of homologues in total, and one or two or more kinds of substances selected from them can be used. The term "derivative" used for the present invention may mean salt, ester, glycoside, or the like, which is acceptable for use in skin external preparations and cosmetics, unless especially indicated. It may be water-soluble or oil-soluble.

Specific examples of tocopherol derivative include tocopherol acetate (d-α-tocopherol acetate or dl-α-tocopherol acetate), tocopherol nicotinate (d-α-tocopherol nicotinate, dl-α-tocopherol nicotinate), tocopherol succinate, tocopheryl phosphate Na, ascorbyl tocopheryl phosphate K, ascorbyl tocopheryl maleate, and so forth. Examples of tocotrienol derivative include tocotrienol acetate, tocotrienol nicotinate, tocotrienol succinate, and so forth. One or two or more kinds of substances selected from these can be used. In the present invention, the ingredient (c) is added for the purpose of imparting firmness and tightness to the skin.

In the present invention, among those mentioned above, tocopherol, tocopherol acetate, and tocopherol nicotinate are preferred, and tocopherol is particularly preferred. Specific examples of commercial product usable as the ingredient (c) include, for example, Riken E Oil 800, Riken E oil 1000 (these are from Riken Vitamin Co., Ltd.), Oryza Tocotrienol 90 (Oryza Oil & Fat Chemical Co., Ltd.), and so forth.

Although content of the ingredient (c) in the liposome composition of the present invention is not particularly limited, it is preferably 0.0005 to 1.0%, more preferably 0.001 to 0.5%, in respect of obtaining a liposome composition showing superior skin firmness and tightness-imparting effect.

Although the present invention relates to the liposome composition appropriately containing the aforementioned ingredient (b) and ingredient (c), a further higher effect can be expected with a specific mass ratio of these ingredients. That is, the mass ratio of the ingredients (b) and (c) ((b)/(c)) is preferably in the range of 0.05 to 9, more preferably in the range of 0.15 to 2. The liposome composition prepared with a mass ratio of the ingredients (b) and (c) within this range shows superior persistency of the moisturizing effect and persistency of the skin firmness and tightness-imparting effect.

Although the ingredients (b) and (c) of the liposome composition of the present invention may be added at the time of the preparation of the liposomes, or added to a cosmetic product obtained after the preparation of the liposomes, it is preferable to add at the time of the preparation of the liposomes in respect of more easily obtaining the effects.

The ingredient (d), polyhydric alcohol, used for the present invention has a structure of having two or more hydroxyl groups in the molecule. In the present invention, the ingredient (d) is an ingredient that can be expected to exhibit an effect as the solvent for dispersing the ingredient (a) in water, and so forth, and is an essential ingredient for preparing a liposome composition that shows superior temporal stability. In the present invention, the liposome composition prepared by using a polyhydric alcohol having an JOB value in the range of 1.5 to 5 shows especially superior skin moisturizing effect. The JOB value is an abbreviation of Inorganic/Organic Balance value, and is a value that represents ratio of inorganic value to organic value, and it serves as an index that indicates degree of polarity of an organic compound. Specifically, the IOB value is defined by the following equation, "IOB value=Inorganic value/Organic value". As for the "inorganic value" and "organic value", specific "inorganic value" and "organic value" are determined for each atom or functional group, for example, an "organic value" of 20 for one carbon atom in a molecule and an "inorganic value" of 100 for one hydroxyl group in a molecule, and an JOB value of an organic compound can be calculated by adding "inorganic values" and "organic values" of all the atoms and functional groups in the organic compound (refer to, for example, Fujita, "Field of Chemistry", volume 11, No. 10, pages 719 to 725, 1957).

In the present invention, the IOB value is in the range of 1.5 to 5, preferably in the range of 1.8 to 5, further preferably in the range of 2 to 5.

The ingredient (d), polyhydric alcohol having an IOB value of 1.5 to 5, is not particularly limited, and examples include, for example, glycerin (IOB value 5.0), 1,3-butylene glycol (IOB value 2.5), dipropylene glycol (IOB value 1.83), propylene glycol (IOB value 3.33), 1,3-propanediol (IOB value 3.33), sorbitol (IOB value 5.0), and so forth. Among these, glycerin, 1,3-butylene glycol, and dipropylene glycol are especially preferred. One kind of the ingredients (d) or an arbitrary combination of two or more kinds of the ingredients (d) may be used, and it is preferable to use two or more kinds of the ingredients (d), in view of persistency of the skin firmness and tightness-imparting effect.

Content of the ingredient (d) in the liposome composition of the present invention is preferably 5 to 30%, more preferably 10 to 25%. With the ingredient (d) of a content within such a range, the liposome composition that shows superior skin moisturizing effect and superior temporal stability of liposomes can be obtained.

The ingredient (e), water, used for the present invention is used as a dispersion medium of the ingredients (a) to (d), and it is not particularly limited, so long as water usually used for cosmetics and the like is used. What is called water such as purified water, deionized water, distilled water, hot spring water, steam distilled water derived from plant such as rose water and lavender water, and so forth can be used.

The ingredient (f), lysophospholipid, used for the present invention is a kind of enzyme-reformed phospholipid, which is obtained by hydrolysis of the ester bond at the position 2 of a phospholipid with a phospholipase. In the present invention, the ingredient (f) is added as an ingredient that forms a bimolecular lipid membrane in the liposome composition, or the like. The ingredient (f), lysophospholipid, is not particularly limited, so long as one used for usual cosmetics is chosen, and specific examples include those obtained by enzyme-reforming of phospholipids mentioned for the ingredient (a), such as soybean lysophospholipids, hydrogenated soybean lysophospholipids, egg yolk lysophospholipids, and hydrogenated egg yolk lysophospholipid. One or two or more kinds of these lysophospholipids may be used as required. Although lysis ratio of the lysophospholipid (ratio of lysophospholipids in the total phospholipids) used in the present invention is not particularly limited, it is preferably 60% or higher, more preferably 80% or higher. Purity of phosphatidylcholine in the lysophospholipid is preferably 20% or higher, more preferably 50% or higher. Specific examples of commercial products include Nikkol Lecinol LL-20 (Nikko Chemicals Co., Ltd.), LP70H (Nippon Fine Chemical Co., Ltd.), Egg Yolk Lysolecithin LPC-1 (Kewpie Corporation), and so forth.

In the liposome composition of the present invention, ratio of contained masses of the ingredient (a) and ingredient (f) ((a)/(f)) is preferably in the range of 10 to 100, more preferably in the range of 15 to 50. With a ratio of contained masses of the ingredient (a) and ingredient (f) within such a range, the liposome composition that shows further superior temporal stability can be obtained.

The ingredient (g), water-soluble polymer (other than the ingredient (b)), used for the present invention is an ingredient that forms hydrogel containing much water around molecules at the time of dissolution of the molecules in water. In the present invention, the ingredient (g) is an ingredient that is expected to improve persistency of the moisturizing effect, or temporal stability of liposomes of a cosmetic product containing the liposome composition. When such a cosmetic product containing the liposome composition is an oil-in-water type emulsion cosmetic product, the ingredient (g) is preferably contained in the aqueous phase as the continuous phase.

As the ingredient (g), water-soluble polymer, described above, any water-soluble polymer used for cosmetics at large can be used without any particular restriction. Specific examples include xanthan gum, carboxymethylcellulose, carboxymethylcellulose sodium, methylcellulose, hydroxymethylcellulose, hydroxyethylcellulose, hydroxypropylcellulose, hydroxypropylmethylcellulose, carboxyvinyl polymer, alkyl-modified carboxyvinyl polymer, *Alcaligenes*-produced polysaccharides, mucopolysaccarides, and so forth. Among these, xanthan gum, *Alcaligenes*-produced polysaccharides, and mucopolysaccarides are more preferred in view of the skin moisturizing effect.

Content of the ingredient (g) in the liposome composition of the present invention is preferably 0.0001 to 2%, more preferably 0.001 to 2%. With the ingredient (g) of a content within such a range as described above, the liposome composition that shows further superior persistency of moisturizing effect and temporal stability of liposomes can be obtained.

As the method for producing the liposome composition of the present invention, a conventional method known to those skilled in the art can be used. Although it is not particularly limited, for example, to a mixture of the ingredients (a) and (c), as well as the ingredient (f), if necessary, prepared beforehand, the ingredients (b), (d), and (e), as well as an aqueous system to be included in the liposomes are added with stirring. Formation of lipid bimolecular membranes in the obtained composition can be confirmed by confirming presence of a Maltese cross image thorough polarizing microscope observation under the cross Nicol condition. Then, by subjecting the obtained composition to a high pressure treatment, the liposome composition that shows further superior temporal stability of liposomes can be obtained. Further, by adding the ingredient (g) and other water-soluble ingredients as required, and mixing them, an aqueous cosmetic product containing the liposome composition can be obtained.

Although mean particle diameter of the liposomes contained in the liposome composition of the present invention is not particularly limited, it is preferably 50 to 400 nm, more preferably 100 to 350 nm, from the viewpoint of temporal stability of liposomes. The liposome composition of the present invention described above may have a transparent or translucent appearance. The values of particle diameter mentioned in this description are those measured with a Coulter counter (Submicron Particle Analyzer N5 produced by Beckman Coulter, Inc.).

In the present invention, the transparent or translucent appearance can be defined as follows. That is, the liposome composition having a transparent or translucent appearance means the composition showing light transmissivity of 30% or higher based on the transmissivity of purified water, which is taken as 100%, as measured with a spectrophotometer at a wavelength of 700 nm using a cell having an optical path length of 10 mm. The spectrophotometer used for measuring the transmissivity was "UV-2500 PC UV-VIS Recording Spectrophotometer" (Shimadzu Corporation).

Although the liposome composition of the present invention can be used as it is, it is preferably used in a state that the liposome composition is contained in a cosmetic product. Since the liposome composition must be dispersed in the cosmetic product mentioned above, the cosmetic product mentioned above is preferably an aqueous cosmetic product. The term "aqueous" means that the cosmetic product is a preparation using water as the medium, which is a preparation advantageous for dispersibility of the liposome composition, but the cosmetic product may contain an oily ingredient. When the liposome composition is used by adding it to a cosmetic product, amount of the liposome composition added to the cosmetic product is not particularly limited. Although the liposome composition itself may be used as a cosmetic product, the liposome composition may be added to a cosmetic product containing an arbitrary ingredient. In such a case, amount of the liposome composition may be 0.1 to 99%, preferably 0.5 to 70%, further preferably 1.0 to 50%, based on the total amount of the cosmetic product. This is because, with an amount of the composition within such a range as described above, a cosmetic product that shows superior persistency of moisturizing effect can be provided.

The liposome composition of the present invention or a cosmetic product containing it may contain, besides the aforementioned ingredients, arbitrary ingredients to be added to usual cosmetics and so forth, such as alcohol, fine particles, film-forming agent, surfactant, oil-soluble gelling agent, organic modified clay mineral, resin, ultraviolet absorbent, preservative, antimicrobial agent, perfume, antioxidant, pH adjustor, and chelating agent, to such an extent that the effect of the present invention is not degraded.

Form of the liposome composition or a cosmetic product containing the same (including the liposome composition itself and a cosmetic product containing the liposome composition) obtained according to the present invention is not particularly limited, and examples of use thereof include, for example, skin care cosmetics such as face toilet, milky lotion, cream, eye cream, essence, massage material, pack material, hand cream, and body cream, and foundation cosmetics. Among these, face toilet to be applied to the face is an aqueous cosmetic product with which the effect of the present invention is easily exhibited, in view of impartation of fresh-looking firmness and tightness to the skin. Examples of the method for using such cosmetics include methods of using them with hand or finger, methods of using them in a state of being impregnated in nonwoven fabric, and so forth.

The liposome composition of the present invention can be used as, besides cosmetics, skin external preparations. Examples of skin external preparations as use of the liposome composition of the present invention include liquid for external use, gel for external use, cream, ointment, liniment, lotion, cataplasm, plaster, spray, aerosol, and so forth. Examples of the method for using them include those mentioned for the cosmetics.

The liposome composition of the present invention and a cosmetic product containing the liposome composition obtained as described above are characterized in that they show superior persistency of moisturizing effect, and superior persistency of skin firmness and tightness-imparting effect, and further show superior temporal stability of liposomes.

The "persistency of moisturizing effect" exhibited by the liposome composition of the present invention and a cosmetic product containing the liposome composition means that moisturized feeling of the skin is maintained even several hours (preferably 10 hours) after application of an objective liposome composition or cosmetic product. The "firmness and tightness" imparted by the liposome composition of the present invention and a cosmetic product containing the liposome composition means that the skin shows such flexible elasticity that the skin is pushed back from the inside thereof:

Presence or absence of the persistency of moisturizing effect, and the firmness and tightness, and degrees thereof can be evaluated by those skilled in the art through a sensory test performed by trained specialists. Such a sensory test can be carried out according to a scoring method. Specifically, objective cosmetics can be evaluated on the basis of averages of scores determined by a plurality of specialists on the basis of scoring criteria determined beforehand.

Example 1

The present invention will be explained in detail with reference to the following examples. The present invention is not limited at all by these examples.

Inventive Products 1 to 18 and Comparative Products 1 to 4 of Liposome Composition Liposome compositions were prepared with the compositions shown in Tables 1 to 3 according to the production method described below. Samples of the compositions were applied to the faces in an appropriate amount by 20 panelists consisting of cosmetics evaluation specialists, evaluated, and scored in 5 grades according to the following evaluation criteria for the items of persistency of moisturizing effect (10 hours after the application), and persistency of skin firmness and tightness-imparting effect (10 hours after the application), and averages of the scores of all of the panelists were calculated, and evaluated in 4 grades according to the following evaluation criteria. Temporal stability of liposomes was also evaluated according to the following evaluation criteria. The results of these evaluations are also shown in Tables 1 to 3.

TABLE 1

| | | | | | Inventive product | | | | | (%) |
|---|---|---|---|---|---|---|---|---|---|---|
| No. | Ingredient | 1 | 2 | 3 | 4 | 5 | 6 | 7 | 8 | |
| 1 | Hydrogenated soybean phospholipids*1 | 1 | 1 | 1 | 1 | 1 | 1 | 1 | — | |
| 2 | Sunflower-derived phospholipids (non-hydrogenated) | — | — | — | — | — | — | — | 1 | |
| 3 | Egg yolk-derived phospholipids (non-hydrogenated) | — | — | — | — | — | — | — | — | |
| 4 | Hydrogenated soybean lysophospholipids*2 | — | — | — | — | — | — | — | — | |
| 5 | *Tremella fuciformis* polysaccharides*3 | 0.01 | 0.01 | 0.01 | 0.01 | 0.01 | 0.01 | 0.01 | 0.01 | |
| 6 | Tocopherol | 0.01 | 0.01 | 0.01 | 0.01 | 0.01 | — | — | 0.01 | |
| 7 | dl-α-Tocopherol acetate | — | — | — | — | — | 0.01 | — | — | |
| 8 | dl-α-Tocopherol nicotinate | — | — | — | — | — | — | 0.01 | — | |
| 9 | 1,3-Butylene glycol (IOB 2.5) | 15 | — | — | 7.5 | 7.5 | 15 | 15 | 15 | |
| 10 | Glycerin (IOB 5) | — | 15 | — | 7.5 | — | — | — | — | |
| 11 | Sorbital (IOB 5) | — | — | 15 | — | — | — | — | — | |
| 12 | Dipropylene glycol (IOB 1.83) | — | — | — | — | 7.5 | — | — | — | |
| 13 | Polypropylene glycol-9 (IOB 0.67) | — | — | — | — | — | — | — | — | |
| 14 | Sodium hyaluronate | — | — | — | — | — | — | — | — | |
| 15 | *Alcaligenes*-produced polysaccharides | — | — | — | — | — | — | — | — | |
| 16 | Xanthan gum | — | — | — | — | — | — | — | — | |
| 17 | Purified water | Balance | Balance | Balance | Balance | Balance | Balance | Balance | Balance | |
| | Contained mass ratio (b)/(c) | 1 | 1 | 1 | 1 | 1 | 1 | 1 | 1 | |
| | Evaluation result | | | | | | | | | |
| | Persistency of moisturzing effect | | | | | | | | | |
| | Score | 3.4 | 3.6 | 3.2 | 4.2 | 4.1 | 4.0 | 3.7 | 4.2 | |
| | Evaluation | + | + | + | ++ | ++ | + | + | ++ | |
| | Persistency of firmness and tightness | | | | | | | | | |
| | Score | 4.1 | 4.1 | 3.5 | 4.2 | 4.1 | 3.9 | 3.8 | 4.3 | |
| | Evaluation | ++ | ++ | + | ++ | ++ | + | + | ++ | |
| | Temporal stability (40° C., 1 month) | + | + | +− | + | + | + | + | + | |

*1PRESOME CS-II 101 (Nippon Fine Chemical Co., Ltd.)
*2LP70H (Nippon Fine Chemical Co., Ltd.)
*3Tremoist-TP (Nippon Fine Chemical Co., Ltd)

TABLE 2

| | | | | | | Inventive product | | | | | | (%) |
|---|---|---|---|---|---|---|---|---|---|---|---|---|
| No. | Ingredient | 9 | 10 | 11 | 12 | 13 | 14 | 15 | 16 | 17 | 18 | 19 |
| 1 | Hydrogenated soybean phospholipids*1 | 1 | 1 | 0.5 | 0.5 | 0.95 | 0.9 | 1 | 1 | 1 | 1 | 1 |
| 2 | Sunflower-derived phospholipids (non-hydrogenated) | — | — | 0.5 | — | — | 0.05 | — | — | — | — | — |
| 3 | Egg yolk-derived phospholipids (non-hydrogenated) | — | — | — | 0.5 | — | — | — | — | — | — | — |
| 4 | Hydrogenated soybean lysophospholipids*2 | — | — | — | — | 0.05 | 0.05 | — | — | — | — | — |
| 5 | *Tremella fuciformis* polysaccharides*3 | 0.001 | 0.018 | 0.01 | 0.01 | 0.01 | 0.01 | 0.01 | 0.01 | 0.01 | 0.01 | 0.001 |

TABLE 2-continued

|  |  | Inventive product (%) | | | | | | | | | | |
|---|---|---|---|---|---|---|---|---|---|---|---|---|
| No. | Ingredient | 9 | 10 | 11 | 12 | 13 | 14 | 15 | 16 | 17 | 18 | 19 |
| 6 | Tocopherol | 0.019 | 0.002 | 0.01 | 0.01 | 0.01 | 0.01 | 0.01 | 0.01 | 0.01 | 0.01 | 0.019 |
| 7 | dl-α-Tocopherol acetate | — | — | — | — | — | — | — | — | — | — | — |
| 8 | dl-α-Tocopherol nicotinate | — | — | — | — | — | — | — | — | — | — | — |
| 9 | 1,3-Butylene glycol (IOB 2.5) | 15 | 15 | 15 | 15 | — | 15 | 15 | 15 | 15 | — | 15 |
| 10 | Glycerin (IOB 5) | — | — | — | — | — | — | — | — | — | — | — |
| 11 | Sorbitol (IOB 5) | — | — | — | — | 15 | — | — | — | — | 15 | — |
| 12 | Dipropylene glycol (IOB 1.83) | — | — | — | — | — | — | — | — | — | — | — |
| 13 | Polypropylene glycol-9 (IOB0.67) | — | — | — | — | — | — | — | — | — | — | — |
| 14 | Sodium hyaluronate | — | — | — | — | — | — | 0.1 | — | — | 0.1 | 0.1 |
| 15 | *Alcaligenes*-produced polysaccharides | — | — | — | — | — | — | — | 0.1 | — | — | — |
| 16 | Xanthan gum | — | — | — | — | — | — | — | — | 0.1 | — | — |
| 17 | Purified water | Balance | Balance | Balance | Balance | Balance | Balance | Balance | Balance | Balance | Balance | Balance |
|  | Contained mass ratio (b)/(c) | 0.05 | 9 | 1 | 1 | 1 | 1 | 1 | 1 | 1 | 1 | 0.05 |
|  | Evaluation result Persistency of moisturizing effect | | | | | | | | | | | |
|  | Score | 3.4 | 3.8 | 4.7 | 4.5 | 3.5 | 4.6 | 4.5 | 4.2 | 3.9 | 3.8 | 3.6 |
|  | Evaluation | + | + | ++ | ++ | + | ++ | ++ | ++ | + | + | + |
|  | Persistency of firmness and tightness | | | | | | | | | | | |
|  | Score | 4.3 | 3.7 | 4.6 | 4.4 | 3.6 | 4.4 | 4.3 | 4.1 | 4.1 | 3.9 | 4.4 |
|  | Evaluation | ++ | + | ++ | ++ | + | ++ | ++ | ++ | ++ | + | ++ |
|  | Temporal stability (40° C., 1 month) | + | + | + | + | + | + | + | + | + | + | + |

*1PRESOME CS-II 101 (Nippon Fine Chemical Co., Ltd.)
*2LP70H (Nippon Fine Chemical Co., Ltd.)
*3Tremoist-TP (Nippon Fine Chemical Co., Ltd.)

TABLE 3

|  |  | Comparative product (%) | | | | |
|---|---|---|---|---|---|---|
| No. | Ingredient | 1 | 2 | 3 | 4 | 5 |
| 1 | Hydrogenated soybean phospholipids*1 | 1 | 1 | 1 | 1 | 1 |
| 2 | Sunflower-derived phospholipids (non-hydrogenated) | — | — | — | — | — |
| 3 | Egg yolk-derived phospholipids (non-hydrogenated) | — | — | — | — | — |
| 4 | Hydrogenated soybean lysophospholipids*2 | — | — | — | — | — |
| 5 | *Tremella fuciformis* polysaccharides*3 | — | 0.01 | 0.01 | 0.01 | — |
| 6 | Tocopherol | 0.01 | — | 0.01 | 0.01 | 0.01 |
| 7 | dl-α-Tocopherol acetate | — | — | — | — | — |
| 8 | dl-α-Tocopherol nicotinate | — | — | — | — | — |
| 9 | 1,3-Butylene glycol (IOB 2.5) | 15 | 15 | — | — | 15 |
| 10 | Glycerin (IOB 5) | — | — | — | — | — |
| 11 | Sorbitol (IOB 5) | — | — | — | — | — |
| 12 | Dipropylene glycol (IOB 1.83) | — | — | — | — | — |
| 13 | Polypropylene glycol-9 (IOB0.67) | — | — | — | 15 | 15 |
| 14 | Sodium hyaluronate | — | — | — | — | 0.01 |
| 15 | *Alcaligenes*-produced polysaccharides | — | — | — | — | — |
| 16 | Xanthan gum | — | — | — | — | — |
| 17 | Purified water | Balance | Balance | Balance | Balance | Balance |
|  | Contained mass ratio (b)/(c) | — | — | 1 | 1 | 1 |
|  | Evaluation result Persistency of moisturizing effect | | | | | |
|  | Score | 2.9 | 3.2 | 1.2 | 2.5 | 2.8 |
|  | Evaluation | +− | + | − | +− | +− |
|  | Persistency of firmness and tightness | | | | | |
|  | Score | 2.8 | 2.2 | 1.1 | 1.9 | 3.1 |
|  | Evaluation | +− | +− | − | − | + |
|  | Temporal stability (40° C., 1 month) | + | + | − | +− | + |

*1PRESOME CS-II 101 (Nippon Fine Chemical Co., Ltd.)
*2LP70H (Nippon Fine Chemical Co., Ltd.)
*3Tremoist-TP (Nippon Fine Chemical Co., Ltd.)

(Production Method)

A: The ingredients (1) to (4), and (6) to (13) were heated to 80° C., and uniformly dissolved.

B: The ingredients (5), and a part of the ingredient (17) were heated to 80° C., and added to the resultant of A, and the mixture was stirred.

C: The resultant of B was cooled, and the ingredients (14) to (16), and the remainder of the ingredient (17) were added thereto.

D: The resultant of C was observed with a polarizing microscope under the cross Nicol condition to confirm the presence of a Maltese cross image, and then subjected to a high pressure treatment (150 MPa, once) in an Altimizer system to obtain a liposome composition.

Each of the samples of the inventive products 1 to 19 and comparative products 1 to 5 obtained by the aforementioned production method was observed with an erecting microscope (Olympus Corporation) under a polarized light at a magnification of 400 times and an exposure time of ½00 second to confirm the presence of a Maltese cross image. Then, each of the samples of the inventive products 1 to 19 and comparative products 1 to 5 was applied to the skins of 20 professional evaluation panelists, and questionnaires were distributed to the panelists for persistency of moisturizing effect (10 hours after the application), and persistency of skin firmness and tightness-imparting effect (10 hours after the application) for evaluation of the products according to the following criteria. Since the liposome composition of the present invention shows, in particular, persistency of the effects, the time between the application and evaluation was set to be 10 hours, and the samples were applied in the morning, and the evaluation was performed in the evening, supposing actual scenes of use.

(1) Persistency of Moisturizing Effect (10 Hours after Application)

5-Grade Absolute Evaluation (Score): (Evaluation)

5: There is superior moisturized feeling on the skin 10 hours after the application.

4: There is moisturized feeling on the skin 10 hours after the application.

3: There is slight moisturized feeling on the skin 10 hours after the application.

2: There is not substantial moisturized feeling on the skin 10 hours after the application.

1: There is completely no moisturized feeling on the skin 10 hours after the application.

4-Grade Evaluation Criteria (Evaluation symbol): (Average of scores)

++: Higher than 4 (very good).

+: Higher than 3 and not higher than 4 (good)

+−: Higher than 2 and not higher than 3 (slightly bad)

−: Not higher than 2 (bad)

(2) Persistency of Firmness and Tightness-Imparting Effect (10 Hours after Application)

5-Grade Absolute Evaluation (Score): (Evaluation)

5: Superior firmness and tightness are felt on the skin 10 hours after the application.

4: Firmness and tightness are felt on the skin 10 hours after the application.

3: Slight firmness and tightness are felt on the skin 10 hours after the application.

2: Substantial firmness and tightness are not felt on the skin 10 hours after the application.

1: Completely no firmness and tightness are felt on the skin 10 hours after the application.

4-Grade Evaluation Criteria (Evaluation symbol): (Average of scores)

++: Higher than 4 (very good).

+: Higher than 3 and not higher than 4 (good)

+−: Higher than 2 and not higher than 3 (slightly bad)

−: Not higher than 2 (bad)

(3) Temporal Stability

Temporal stability of the prepared samples was evaluated by leaving the samples standing at 40° C. for one month, and then observing them with a transmission electron microscope (TEM). Evaluation was made according to the following evaluation criteria.

+: Liposomes are confirmed.

+−: Liposomes lacking parts thereof are confirmed.

−: Liposomes are not confirmed.

The liposome compositions of the inventive products 1 to 19 showed superior persistency of the moisturizing effect (10 hours after the application), superior persistency of the skin firmness and tightness-imparting effect (10 hours after the application), and superior temporal stability of liposomes. The inventive products 11, 12, and 14 containing the non-hydrogenated phospholipids and the hydrogenated phospholipids showed especially superior persistency of the moisturizing effect and persistency of the firmness and tightness-imparting effect, and among these, the inventive products 11 and 14 containing the sunflower-derived phospholipids showed further higher effects.

On the other hand, the comparative product 1 not containing the ingredient (b) was evaluated to be poor for persistency of the moisturizing effect and persistency of the skin firmness and tightness-imparting effect. The comparative product 2 not containing the ingredient (c) was evaluated to be poor for persistency of the skin firmness and tightness-imparting effect. The comparative product 3 not containing the ingredient (d) was evaluated to be poor for the temporal stability of liposomes, and evaluated to be extremely poor for persistency of the moisturizing effect and persistency of the skin firmness and tightness-imparting effect. These results demonstrated that, according to the present invention, the ingredients (b), (c), and (d) are indispensable ingredients, and if any one of these is lacked, the effect of the present invention cannot be obtained.

The comparative product 4 containing the polyhydric alcohol having an IOB value of 0.67 showed poor persistency of the moisturizing effect and poor persistency of the skin firmness and tightness-imparting effect. While a higher IOB value means higher hydrophilicity, it is considered that the polyhydric alcohol having an IOB value in the range of 1.5 to 5 is highly compatible with water in the liposome composition, and easily retained in the skin together with liposomes to exhibit the effect of the present invention. That is, by the above results, it was demonstrated that the ingredient (d) needs to have a specific IOB value.

Example 2: Aqueous Cosmetic Product (Face Toilet)

|  | (Ingredient) | (%) |
| --- | --- | --- |
| 1. | Hydrogenated soybean phospholipids | 2 |
| 2. | Hydrogenated soybean lysophospholipids | 0.1 |
| 3. | Cholesterol | 0.3 |
| 4. | Tocopherol | 0.005 |
| 5. | Astaxanthin*4 | 0.01 |
| 6. | Glycerin | 5 |

-continued

| | (Ingredient) | (%) |
|---|---|---|
| 7. | 1,3-Butylene glycol | 15 |
| 8. | *Tremella fuciformis* polysaccharides | 0.01 |
| 9. | Purified water | Balance |
| 10. | Clove extract | 0.1 |
| 11. | Edelweiss extract | 0.1 |
| 12. | White birch extract | 0.1 |
| 13. | Sandalwood extract | 0.1 |
| 14. | Hydrolyzed collagen | 0.1 |

*4Astaxanthin 5C (*Oryza* Oil & Fat Chemical Co., Ltd.)

(Production Method)
A: The ingredients (1) to (7) were heated to 80° C., and uniformly dissolved.
B: The ingredient (8) and a part of the ingredient (9) were heated to 80° C., and added to the resultant of A, and the mixture was stirred.
C: The resultant of B was cooled, observed with a polarizing microscope under the cross Nicol condition to confirm the presence of a Maltese cross image, and then subjected to a high pressure treatment (200 MPa, once) in an Altimizer system.
D: The ingredients (10) to (14), and the remainder of the ingredient (9) were added to the resultant of C, and they were mixed to obtain an aqueous cosmetic product (face toilet).

The aqueous cosmetic product of Example 2 (face toilet) showed superior persistency of the moisturizing effect (10 hours after the application), superior persistency of the skin firmness and tightness-imparting effect (10 hours after the application), and superior temporal stability of liposomes.

Example 3: Aqueous Cosmetic Product (Gel)

| | (Ingredient) | (%) |
|---|---|---|
| 1. | Hydrogenated soybean phospholipids | 3 |
| 2. | Sunflower phospholipids | 0.1 |
| 3. | Cholesterol | 0.3 |
| 4. | Tocopherol | 0.01 |
| 5. | 1,3-Butylene glycol | 15 |
| 6. | *Tremella fuciformis* polysaccharides | 0.01 |
| 7. | Purified water | Balance |
| 8. | Xanthan Gum | 0.05 |
| 9. | Carbomer | 0.1 |
| 10. | Sodium hydroxide | Optimum amount |
| 11. | Hydroxyproline | 0.05 |
| 12. | Cytocatalyzer | 0.05 |
| 13. | Sodium hyaluronate | 0.05 |

(Production Method)
A: The ingredients (1) to (5) were heated to 80° C., and uniformly dissolved.
B: The ingredient (6) and a part of the ingredient (7) were heated to 80° C., and added to the resultant of A, and the mixture was stirred.
C: The resultant of B was cooled, observed with a polarizing microscope under the cross Nicol condition to confirm the presence of a Maltese cross image, and then subjected to a high pressure treatment (80 MPa, 2 times) in a Microfluidizer system.
D: The ingredients (8) to (13), and the remainder of the ingredient (7) were added to the resultant of C, and they were mixed to obtain an aqueous cosmetic product (gel).

The aqueous cosmetic product of Example 3 (gel) showed superior persistency of the moisturizing effect (10 hours after the application), superior persistency of the skin firmness and tightness-imparting effect (10 hours after the application), and superior temporal stability of liposomes.

Example 4: Aqueous Cosmetic Product (Body Mist)

| | (Ingredient) | (%) |
|---|---|---|
| 1. | Hydrogenated soybean phospholipids | 0.5 |
| 2. | Hydrogenated soybean lysophospholipids | 0.01 |
| 3. | Cholesterol | 0.01 |
| 4. | Ceramide II | 0.001 |
| 5. | Ceramide III | 0.001 |
| 6. | Tocopherol | 0.01 |
| 7. | 1,3-Butylene glycol | 5 |
| 8. | Dipropylene glycol | 15 |
| 9. | *Tremella fuciformis* polysaccharides | 0.01 |
| 10. | Purified water | Balance |
| 11. | Rosemary extract | 0.01 |
| 12. | Lily extract | 0.01 |
| 13. | Ginger root extract | 0.01 |

(Production Method)
A: The ingredients (1) to (8) are heated to 100° C., and uniformly dissolved.
B: The ingredient (9), and a part of the ingredient (10) were heated to 80° C., and added to the resultant of A, and the mixture was stirred.
C: The resultant of B was cooled, observed with a polarizing microscope under the cross Nicol condition to confirm the presence of a Maltese cross image, and then subjected to a high pressure treatment in an Altimizer system.
D: The ingredients (11) to (13), and the remainder of the ingredient (10) were added to the resultant of C, and they were mixed to obtain an aqueous cosmetic product (body mist).

The aqueous cosmetic product of Example 4 (body mist) showed superior persistency of the moisturizing effect (10 hours after the application), superior persistency of the skin firmness and tightness-imparting effect (10 hours after the application), and superior temporal stability of liposomes.

Example 5: Aqueous Cosmetic Product (Essence)

| | (Ingredient) | (%) |
|---|---|---|
| 1. | Hydrogenated soybean phospholipids | 3 |
| 2. | Sunflower phospholipids | 0.1 |
| 3. | Cholesterol | 0.3 |
| 4. | Tocopherol | 0.01 |
| 5. | Linoleic acid | 0.1 |
| 6. | 1,3-Butylene glycol | 8 |
| 7. | Dipropylene glycol | 7 |
| 8. | *Tremella fuciformis* polysaccharides | 0.01 |
| 9. | Purified water | Balance |
| 10. | Xanthan Gum | 0.1 |
| 11. | *Alcaligenes*-produced polysaccharides | 0.002 |
| 12. | Dipotassium glycyrrhizinate | 0.1 |
| 13. | Theanine | 0.01 |

(Production Method)
A: The ingredients (1) to (7) were heated to 80° C., and uniformly dissolved.
B: The ingredient (8), and a part of the ingredient (9) were heated to 80° C., and added to the resultant of A, and the mixture was stirred.

C: The resultant of B was cooled, observed with a polarizing microscope under the cross Nicol condition to confirm the presence of a Maltese cross image, and then subjected to a high pressure treatment (80 MPa, 2 times) in a Microfluidizer system.

D: The ingredients (10) to (13), and the remainder of the ingredient (9) were added to the resultant of C, and they were mixed to obtain an aqueous cosmetic product (essence).

The aqueous cosmetic product of Example 5 (essence) showed superior persistency of the moisturizing effect (10 hours after the application), superior persistency of the skin firmness and tightness-imparting effect (10 hours after the application), and superior temporal stability of liposomes.

The invention claimed is:

1. A liposome comprising the following ingredients (a) to (e):
   (a) A phospholipid
   (b) A *Tremella fuciformis* extract
   (c) Vitamin E or a derivative thereof
   (d) A polyhydric alcohol having an IOB value of 1.5 to 5
   (e) Water,
   wherein the ingredient (d) consists of one or more selected from the group consisting of 1,3-butylene glycol, glycerin, and dipropylene glycol, and
   wherein content of the ingredient (d) contained in the liposome is in the range of 10 to 25%.

2. The liposome according to claim 1, wherein mass ratio of the ingredients (b) and (c) ((b)/(c)) contained in the liposome is in the range of 0.05 to 9.

3. The liposome according to claim 1, further comprising a lysophospholipid as an ingredient (f).

4. A cosmetic product containing the liposome according to claim 1.

5. The cosmetic product according to claim 4, wherein the cosmetic product consists of an oil-in-water type emulsion, and contains a water-soluble polymer (other than the ingredient (b)) as an ingredient (g) in an aqueous layer as a continuous phase.

6. The liposome according to claim 1, wherein the ingredient (a) contains a phospholipid derived from sunflower.

* * * * *